United States Patent [19]

Laakso et al.

[11] Patent Number: 5,227,396
[45] Date of Patent: Jul. 13, 1993

[54] INDOLE ANTIINSECTAN METABOLITES

[75] Inventors: Jodi A. Laakso, Iowa City, Iowa; Mark R. TePaske; Patrick F. Dowd, both of Peoria, Ill.; James B. Gloer, Iowa City, Iowa; Donald T. Wicklow, Peoria, Ill.; Gail M. Staub, Madison, Wis.

[73] Assignees: The United States of America as represented by the Secretary of Agriculture, Washington, D.C.; University of Iowa Research Foundation, Iowa City, Iowa; Biotechnology Research & Development Corporation, Peoria, Ill.

[21] Appl. No.: 875,360

[22] Filed: Apr. 29, 1992

Related U.S. Application Data

[63] Continuation-in-part of Ser. No. 732,786, Jul. 19, 1991, Pat. No. 5,130,326.

[51] Int. Cl.$^5$ .................... A01M 43/90; C07D 209/94
[52] U.S. Cl. .................................... 514/410; 540/462; 548/417
[58] Field of Search ......................... 548/417; 514/410

[56] References Cited

U.S. PATENT DOCUMENTS

| | | | |
|---|---|---|---|
| 4,356,330 | 10/1982 | Cuscurida | 568/756 |
| 4,973,601 | 11/1990 | Dowd et al. | 514/410 |
| 5,017,598 | 5/1991 | Dowd et al. | 514/415 |
| 5,068,349 | 11/1991 | Kanda et al. | 548/418 |

OTHER PUBLICATIONS de Jesus et al. "Tremorgenic Mycotoxins from *Penicillin crustosum.*" *J. Chem. Soc. Perkin Trans I*, (1983) pp. 1847-1856 and 1859 to 1861.

Gallagher, R. T. and Clardy, J. "Aflatrem, A Tremorgenic Toxin from *Asperqillus flavus.*" *Tetrahedron Lett.*, vol. 21, (1980) pp. 239-242.

Springer, J. P. and Clardy, J. "Paspaline and Paspalicine, Two Indole-Mevalonate Metabolites From *Claviceps Paspali.*" *Tetrahedron Lett.*, vol. 21, (1980), pp. 231-234.

Gallagher et al. "Paspalinine, A Tremogenic Metabolite From *Claviceps paspali* Stevens Et Hall," *Tetrahedron Lett.*, vol. 21, (1980), pp. 235-238.

Wicklow, et al., Trans. Br. mycol. Soc., 91 pp. 433-438, (1988).

Primary Examiner—Joseph Paul Brust
Attorney, Agent, or Firm—Arnold, White & Durkee

[57] ABSTRACT

Sulpinine C, secopenitrem B and 10-oxo-11,33-dihydropenitrem B indole compounds have been isolated from the sclerotia of the fungi *Aspergillus sulphureus*. Aflatrem B has been isolated from the sclerotia of the fungi *Aspergillus flavus*, and 14-hydroxypaspalinine and 14-(N,N-dimethylvalyloxy)paspalinine have been isolated from the sclerotia of the fungi *Aspergillus nomius*. The indole compounds are effective for controlling Coleopteran and Lepidopteran insects.

7 Claims, No Drawings

INDOLE ANTIINSECTAN METABOLITES

This is a continuation-in-part of copending U.S. patent application Ser. No. 07/732,786 filed Jul. 19, 1991, now U.S. Pat. No. 5,130,326.

BACKGROUND OF THE INVENTION

1. Field of the Invention

The present invention is generally related to indole compounds. More specifically, the indole compounds are used as insecticides for control of Lepidoptera and Coleoptera species.

2. Background of the Art

Certain fungi produce specialized resting bodies known as sclerotia as a means for surviving adverse environmental conditions which other fungal bodies cannot tolerate, such as harsh climate, nutrient deficiency and desiccation. Generally, sclerotia remain viable in soil for periods of several years, and provide primary inoculum for the producing species when conditions again become favorable for fungal growth. Sclerotia are formed under natural conditions or in solid substrate fermentations, but are not commonly produced in the liquid fermentation cultures generally employed in studies of microbial metabolites. Accordingly, many novel sclerotial metabolites of common fungi such as Aspergillus have not been characterized.

While sclerotia are known to contain biologically active secondary metabolites not found in other fungal parts or in liquid cultures, study of sclerotia as sources of novel metabolites has been limited. Investigation of large sclerotia (ergots) of *Claviceps purpurea* led to the discovery and medicinal use of ergot alkaloids.

Sclerotia have recently been recognized as a valuable potential source for natural antiinsectans. Many sclerotia, which are subjected to predation by fungivorous insects and arthropods during their period of dormancy in soil, have been shown to contain metabolites that exert adverse physiological effects on insects. Gloer et al. [*J. Org. Chem.* 53:5457 (1988)] and Wicklow et al. [*Trans. Br. Mycol. Soc.* 91:433 (1988)] disclose the isolation of four antiinsectan aflavanine derivatives from the sclerotia of *Aspergillus flavus* for use in controlling the dried-fruit beetle *Carpophilus hemipterus* (Nitidulidae:-Coleoptera). TePaske et al. [*J. Org. Chem.* 55:5299 (1990)] disclose a related metabolite, aflavazole, which was isolated from extracts of *A. flavus* sclerotia. Gloer et al. [*J. Org. Chem.* 54:2530 (1989)] describe an insecticidal indole diterpene known as nominine found only in the sclerotia of *Aspergillus nomius* for the control of the corn earworm *Helicoperva zea* (Lepidoptera), formerly *Heliothis zea*. Nominine is also disclosed by Dowd et al. in U.S. Pat. No. 5,017,598 issued May 21, 1991, and entitled "Nominine, an Insecticidal Fungal Metabolite".

The compounds penitrem A-F [de Jesus et al., *J. Chem. Perkin Trans. I*, 1847-1861 (1983)] and aflatrem [Gallagher et al., *Tetrahedron Lett.* 21:239 (1980)] are known tremorgenic mycotoxins which are produced from strains of *Penicillium crustosum* and *Aspergillus flavus*, respectively. Paspalinine, paspalicine and paspaline from *Claviceps paspali* are also known to cause tremors in mice and domestic animals [Gallagher et al., *Tetrahedron Lett.* 21:235 (1980); Springer and Clardy, *Tetrahedron Lett.* 21:231 (1980)]. A mechanism of action for these tremorgens is proposed by Setala et al., *Drug Chem. Toxicol.* 12:237 (1989).

Tremorgenic mycotoxins such as penitrem A, aflatrem and paspaline are described by Dowd et al. as possessing insecticidal activity [U.S. Pat. No. 4,973,601, issued Nov. 27, 1990; *J. Antibiot.* 41:1868 (1988)] Dowd et al. disclose a method of controlling insects such as *H. zea* and *S. frugiperda* by applying a fungal tremorgenic metabolite containing an indole moiety to a locus of insects.

There remains a continuing need for new insecticides because many agriculturally important insect species have developed a resistance to the most potent insecticides which are currently available. Moreover, environmentally tolerable replacements for these insecticides are declining. New natural, biodegradable insecticides which are relatively nontoxic to vertebrates and may be produced by fermentation processes are a cost effective replacement for known insecticides.

SUMMARY OF THE INVENTION

In order to satisfy the need for a cost effective, natural, biodegradable insecticide, one aspect of the present invention provides substantially pure indole compounds which are effective for controlling Lepidopteran and Coleopteran insects. Sulpinine C has the structure:

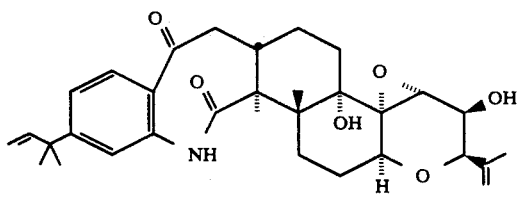

secopenitrem B has the formula:

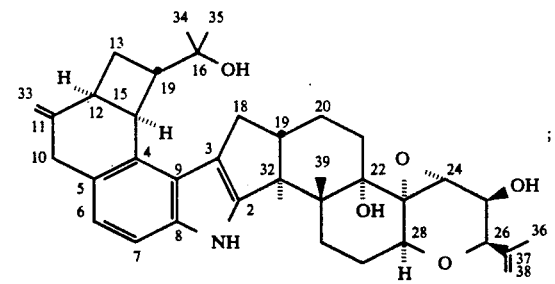

aflatrem B has the structure:

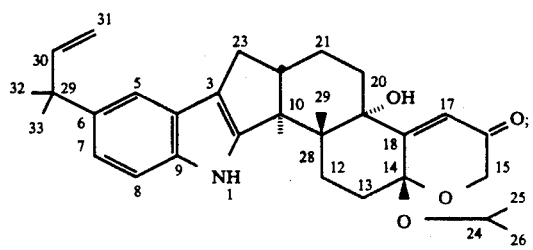

14-hydroxypaspalinine has the structure:

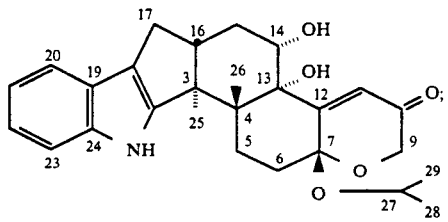

14-(N,N-dimethylvalyloxy)paspalinine has the formula:

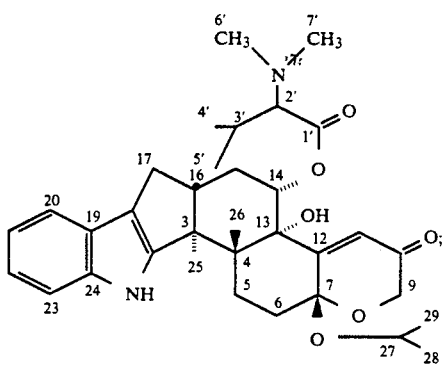

and 10-oxo-11,33-dihydropenitrem B has the formula:

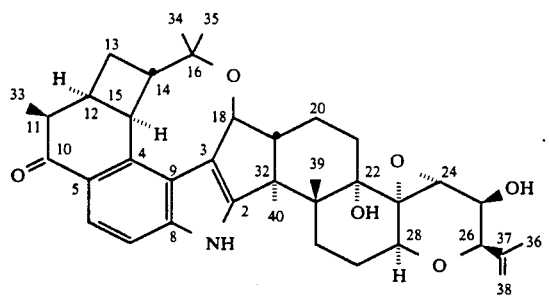

Another aspect of the present invention provides a composition for controlling insects containing a sulpinine C, aflatrem B, secopenitrem B, 14-hydroxypaspalinine, 14-(N,N-dimethylvalyloxy)paspalinine, or 10-oxo-11,33-dihydropenitrem B compound and an inert carrier. The compound is preferably present in the composition in an amount effecting insects of the Lepidopteran or Coleopteran species, such as *Helicoverpa zea* or *Carpophilus hemipterus*. An effective amount of the composition may be applied to a locus of insects in order to control the insects.

DETAILED DESCRIPTION OF THE INVENTION

The present invention provides several substantially pure indole compounds effective in controlling insects, insecticidal compositions containing a compound of the present invention and a method for controlling insects by applying the compositions to the locus of the insects. The compounds of the present invention have been designated sulpinine C, aflatrem B, secopenitrem B, 14-hydroxypaspalinine, 14-(N,N-dimethylvalyloxy)paspalinine, and 10-oxo-11,33-dihydropenitrem B, and are collectively referred to as "the compounds."

Sulpinine C, secopenitrem B and 10-oxo-11,33-dihydropenitrem B are isolated from the sclerotia of the fungus *Aspergillus sulphureus*, a member of the *A. ochraceus* taxonomic group. 14-Hydroxypaspalinine and 14-(N,N-dimethylvalyloxy)paspalinine, and aflatrem B are isolated from the sclerotia of the fungus *Aspergillus nomius* and *Aspergillus flavus*, respectively. Strains of the fungi *Aspergillus sulphureus*, *Aspergillus flavus* and *Aspergillus nomius* were deposited on Jun. 11, 1991, Jun. 10, 1991, and Dec. 19, 1989 respectively, in the Agricultural Research Service Patent Culture Collection (NRRL) in Peoria, Ill. and have been assigned respective Deposit Nos. NRRL 18838, 18835 and 18585. The culture deposit will be stored and made available to the public in accord with the provisions of the Budapest Treaty for the Deposit of Microorganisms. All restrictions on the availability of the culture deposit to the public will be irrevocably removed upon the granting of a patent disclosing the strain.

The sclerotia of *A. sulphureus*, *A. flavus* and *A. nomius* are produced by solid-substrate fermentation on corn kernels. They are ground by conventional means to a suitable particle size and are extracted with at least one solvent. Suitable solvents for the extraction could be readily determined by the skilled artisan and would include any solvents in which the compounds of the present invention are soluble. Preferably, the ground sclerotia of *A. sulphureus* are sequentially extracted with pentane and methylene chloride. The ground sclerotia of *A. flavus* are extracted with hexane. *A. nomius* sclerotia are preferably extracted with pentane to extract 14-(N,N-dimethylvalyloxy)paspalinine, and are sequentially extracted with hexane and chloroform to extract 14-hydroxypaspalinine.

Isolation and purification of the compounds of the present invention from the solvent extract is effected by the use of conventional techniques, such as high-performance liquid chromatography (HPLC), thin layer chromatography (TLC), silica gel column chromatography and countercurrent distribution (CCD). In a preferred embodiment of the invention, a solvent extract is separated by silica gel column chromatography, and the resulting fraction is further separated by reversed-phase HPLC. Sulpinine C, secopenitrem B and 10-oxo-11,33-dihydropenitrem B are isolated using this procedure as described in Examples 1 and 6, although the procedure is not limited thereto. In another preferred embodiment described in Examples 4 and 8, solvent extracts are subjected to reversed-phase HPLC to yield aflatrem B, 14-hydroxypaspalinine and 14-(N,N-dimethylvalyloxy)paspalinine.

Commercial formulations including the compounds of the present invention may be prepared directly from fungal extracts or from the fractions derived from the extracts. However, the formulations are prepared from a pure or a substantially pure compound when a high degree of specificity is required. For example, if a high degree of predictability of the intended response by both target and nontarget species is required, a formulation prepared from a pure or substantially pure form of a compound of the present invention would be used. The formulation would then exclude other substances found in natural fungi which might have an adverse effect on activity or a toxic effect toward nontarget species.

Insecticidal compositions of the present invention include sulpinine C, aflatrem B, secopenitrem B, 14-hydroxypaspalinine, 14-(N,N-dimethylvalyloxy)paspalinine, or 10-oxo-11,33-dihydropenitrem B as described above in combination with a suitable inert carrier as known in the art. Agronomically acceptable carriers such as alcohols, ketones, esters and surfactants are illustrative. A compound of the present invention is present in the composition in an amount effecting the target species which is typically at least about 1.0 ppm. The concentration of the compound in an insecticidal composition will vary considerably depending upon the target species, substrate, method of application and desired response. Addition factors to be considered in determining an optimum concentration include phytotoxicity toward the treated plant and the tolerance of nontarget species.

The compounds of the present invention act to control pests by mechanisms including growth regulation, death inducement, sterilization, as well as interference with metamorphosis and other morphogenic functions. The resulting response is dependant on the pest species, the compound concentration and method of application. The compound is administered in an amount effecting one or more of the responses as may be predetermined by routine testing. Where the intended response is pest mortality, an "effective amount" is defined as the quantity of the compound which will effect a significant mortality rate of a test group as compared with an untreated group. The actual effective amount will vary with the species of pest, stage of larval development, nature of the substrate, the type of inert carrier, the period of treatment and other related factors.

The compositions of the present invention are effective in controlling a variety of insects. Agronomically important insects such as those of the orders Lepidoptera and Coleoptera are of particular interest. However, the compounds and compositions of the present invention are not limited thereto.

The insecticidal compositions of the present invention are used to control insects by applying the composition to the locus of the pest to be controlled. When the compound is intended as a stomach poison, it is applied in conjunction with an inert carrier to the pest diet. The composition is applied to plants by treating the leaf surfaces or by systematic incorporation. As a contact poison, any topical method of application will be effective, such as direct spraying on the pest or on a substrate which is likely to be contacted by the pest.

The following examples are presented to describe preferred embodiments and utilities of the present invention and are not meant to limit the present invention unless otherwise stated in the claims appended hereto.

EXAMPLE 1

Isolation and Purification of Sulpinines A-C and Secopenitrem B

The culture of *A. sulphureus* (NRRL 18838) was obtained from the Agricultural Research Service (ARS) culture collection at the National Center for Agricultural Utilization Research in Peoria, Ill. Production of sclerotia was accomplished by solid substrate fermentation of *A. sulphureus* on autoclaved corn kernels using procedures described by Wicklow et al., supra (1988). The sclerotia were harvested, ground to a powder using a Tecator mill obtained from Perstorp Instrument Co. and stored at 4° C. until extraction.

Powdered sclerotia of *A. sulphureus* (150.0 g) were sequentially extracted with pentane and methylene chloride using a Soxhlet apparatus. A portion (894 mg) of the total methylene chloride extract (1.59 g) was fractionated by silica gel column chromatography. A stepwise gradient from 0-10% (v/v) methanol in chloroform was employed resulting in the elution and collection of a distinct red band at 4% methanol. This active fraction (105.2 mg) was further separated by reversed-phase HPLC (89:11 MeOH-H$_2$O) to yield 4.3 mg penitrem B, 18.0 mg sulpinine A, 4.1 mg sulpinine B, 4.0 mg sulpinine C, and 10.2 mg secopenitrem B.

In determining the properties of the compounds, proton NMR and heteronuclear multiple bond correlation (HMBC) data were obtained on a Bruker AMX-600 spectrometer. $^{13}$C NMR data was obtained using Bruker AC-300 or WM-360 spectrometers. Heteronuclear multiple quantum correlation (HMQC) experiments were conducted using MSL-300 or AMX-600 spectrometers. All spectra were recorded in CDCl$_3$, acetone-d$_6$, or CD$_3$OD, and chemical shifts were referenced using the corresponding solvent signals: 7.24 ppm/77.0 ppm, 2.04 ppm/29.8 ppm, or 3.30 ppm/49.0 ppm, respectively. Multiplicities of carbon signals were determined through distortionless enhancement by polarization transfer (DEPT) experiments. Selective insensitive nuclei enhanced by polarization transfer (INEPT) experiments were optimized for $^n J_{CH}$ values of 4, 7 or 10 Hz, while the HMBC experiments were optimized for $^n J_{CH} = 8.3$ Hz. A VG TRIO-1 mass spectrometer equipped with a direct inlet probe was used to obtain EI mass spectra at 70 eV. High resolution electron impact mass spectrometry (HREIMS) data were acquired with a VG ZAB-HF instrument. HPLC separations were accomplished using a Beckman Ultrasphere ODS column (5-μm particles, 250 × 10 mm) at a flow rate of 2.5 ml/min; UV detection was at 215 nm. Penitrem B has an HPLC retention time under the above conditions of 20.1 min.

Sulpinine A has the following properties: HPLC retention time 16.0 min; $^1$H NMR, $^{13}$C NMR, HMQC, and selective INEPT data in Table 1; electron impact mass spectrometry (EIMS): 503 (M+; rel. int. 31.6), 488 (43), 467 (12), 452 (13), 434 (10), 397 (10), 373 (24), 358 (29), 250 (100), 222 (35), 198 (33), 182 (72), 167 (21); HREIMS: obsd. 503.3039; calcd. for C$_{32}$H$_{41}$NO$_4$, 503.3035. Sulpinine A has the structure:

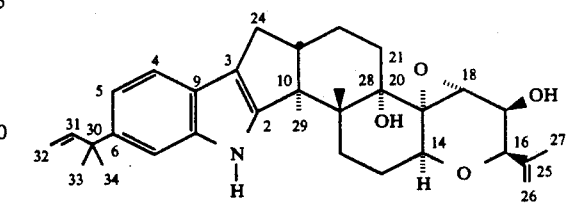

TABLE 1

| NMR Spectral Data For Sulpinine A$^a$ | | | |
|---|---|---|---|
| C/H# | $^1$H | $^{13}$C | Selective INEPT Correlations |
| 2 | — | 153.87 | |
| 3 | — | 116.67 | |
| 4 | 7.20(d; 8.3) | 118.12 | 3, 6, 8, 9 |
| 5 | 6.95(dd; 8.3, 1.7) | 118.6 | 7, 9, 30 |
| 6 | — | 141.96 | |
| 7 | 7.28(d; 1.3) | 110.02 | 5, 6, 8, 9, 30 |
| 8 | — | 141.22 | |
| 9 | — | 124.37 | |
| 10 | — | 52.02 | |
| 11 | —. | 43.76 | |
| 12 | 1.63(m), 2.6(m) | 27.36 | |
| 13 | 2.09(m), 2.25(m) | 29.07 | 12, 14 |

TABLE 1-continued

NMR Spectral Data For Sulpinine A[a]

| C/H# | $^1$H | $^{13}$C | Selective INEPT Correlations |
|---|---|---|---|
| 14 | 4.28(br dd; 9.0, 8.8) | 72.08 | 13, 18, 19 |
| 15 | — | — | |
| 16 | 4.04(br s) | 75.08 | |
| 17 | 4.025(br d; 3.1) | 66.54 | |
| 18 | 3.47(br d; 2.0) | 66.26 | 16, 17, 19 |
| 19 | — | 66.79 | |
| 20 | — | 78.83 | |
| 21 | 1.37(m), 1.60(m) | 27.17 | |
| 22 | 1.49(d m; 10.0), 1.89(dddd; 12, 12, 12, 3) | 21.94 | 10, 23 |
| 23 | 2.69(m) | 51.5 | 2, 10, 11, 22, 29 |
| 24 | 2.32(m), 2.56(m) | 30.53 | |
| 25 | — | 143.19 | |
| 26 | 4.91(br s), 5.10(br s) | 111.91 | |
| 27 | 1.70(br s) | 19.76 | |
| 28 | 1.14(s) | 19.05 | 10, 11, 12, 20 |
| 29 | 1.26(s) | 16.46 | 2, 10, 11, 23 |
| 30 | — | 42.08 | |
| 31 | 6.07(dd; 17.6, 10.6) | 150.54 | 8, 30, 33, 34 |
| 32 | 4.97(dd; 10.6, 1.5) 5.07(dd; 17.5, 1.5) | 110.16 | |
| 33 | 1.41(s) | 29.3 | |
| 34 | 1.41(s) | 29.3 | |

[a]Data were recorded in methanol-$d_4$ at 600 and 75.6 MHz, respectively. All selective INEPT correlations represent 2- or 3-bond couplings.

Sulpinine B had an HPLC retention time of 13.8 min; $^1$H NMR, $^{13}$C NMR, HMQC, and selective INEPT data in Table 2; EIMS: 487 (M+, rel. int. 21), 472 (16), 469 (10), 451 (26), 436 (11), 250 (100), 198 (34), 182 (71), 167 (23), 129 (45), 115 (28), 105 (21); HREIMS: obsd. 487.3104, calcd. for $C_{32}H_{41}NO_3$, 487.3086. Sulpinine B has the structure:

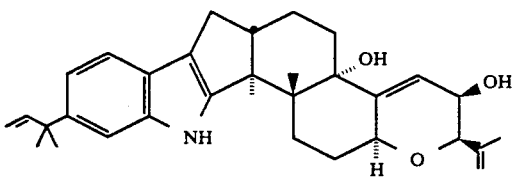

Sulpinine C has the properties: HPLC retention time 6.0 min; $^1$H NMR, $^{13}$C NMR, HMQC, and HMBC data in Table 3; EIMS: 535 (M+rel. int. 13), 254 (3), 242 (3), 228 (3), 214 (11), 200 (4), 188 (100), 172 (5), 145 (9), 130 (9), 115 (5.3), 105 (6); HREIMS: obsd. 535.2946; calcd. for $C_{32}H_{41}NO_6$, 535.2933.

Secopenitrem B has the following properties: HPLC retention time 8.5 min; EIMS: 585 (M+, rel. int. 4), 567 (11), 552 (17), 531 (6), 516 (7), 499 (84), 484 (40), 437 (32.5), 422 (35), 369 (23), 354 (26), 314 (70), 301 (31), 246 (100), 233 (37), 194 (38). $^1$H NMR (CDCl$_3$): H-6, 6.88 (d; 8.1); H-7, 7.07 (d; 8.1); H-10, 3.90 (br d; 15.1), 3.40 (d; 15.3); H-12, 3.15 (dd; 8.9, 8.8); H-13, 2.33 (m), 1.85 (m); H-14, 2.48 (m); H-15, 4.075 (dd; 8.5, 8.7); H-18, 2.99 (dd; 13.0, 6.1), 2.47 (m); H-19, 2.75 (m); H-20, 1.89 (m), 1.62 (m); H-21, 1.53 (m), 1.50 (m); H-24, 3.64 (d; 2.3); H-25, 4.03 (br s); H-26, 4.10 (br s); H-28, 4.30 (dd; 9,9); H-29, 2.36 (m), 1.93 (m); H-30, 2.67 (ddd; 13.6, 13.6, 5.1), 1.33 (m); H-33, 4.83 (br s), 4.72 (br s); H$_3$-34, 1.16 (s); H$_3$-35, 1.07 (s); H$_3$-36, 1.72 (br s); H-38, 5.16 (br s), 5.02 (br s); H$_3$-39, 1.163 (s); H$_3$-40, 1.176 (s). $^{13}$C NMR (CDCl$_3$): C-2, 151.98; C-3, 116.25; C-4, 131.34; C-5, 129.67; C-6, 121.1; C-7, 109.33; C-8, 123.38; C-9, 138.94; C-10, 37.62; C-11, 149.21; C-12, 36.46; C-13, 25.84; C-14, 52.29; C-15, 36.98; C-16, 71.38; C-18, 29.4; C-19, 49.85; C-20, 20.48; C-21, 30.20; C-22, 77.96; C-23, 65.83; C-24, 61.82; C-25, 64.68; C-26, 73.63, C-28, 71.54; C-29, 27.73; C-30, 27.41; C-31, 42.37; C-32, 50.20; C-33, 108.33; C-34, 26.46; C-35, 27.32; C-36, 19.48; C-37, 141.13; C-38, 112.34; C-39, 18.64; C-40, 15.63. High resolution fast atom bombardment mass spectrometry (HRFABMS): obsd. 586.3589; calcd. for $C_{37}H_{47}NO_5$, 585.3454.

TABLE 2

NMR Spectral Data For Sulpinine B[a]

| C/H# | $^1$H | $^{13}$C | Selective INEPT Correlations |
|---|---|---|---|
| 1 | 7.72(br s) | — | 2, 3, 8, 9 |
| 2 | — | 152.21 | |
| 3 | — | 116.93 | |
| 4 | 7.34(d; 8.3) | 117.93 | 3, 6, 8, 9 |
| 5 | 7.07(dd; 8.3, 1.5) | 118.5 | 7, 9, 30 |
| 6 | — | 141.24 | |
| 7 | 7... .(d; 0.8) | 108.89 | 5, 6, 8, 9, 30 |
| 8 | — | 139.75 | |
| 9 | — | 123.06 | |
| 10 | — | 50.73 | |
| 11 | — | 42.86 | |
| 12 | 2.68(d m; 6.0), 1.59(m) | 28.24 | |
| 13 | 2.23(m), 1.84(m) | 29.26 | |
| 14 | 4.61(br dd; 9.1, 8.8) | 73.65 | 12, 18, 19 |
| 16 | 3.86(br s) | 79.07 | 14, 25, 26, 27 |
| 17 | 3.96(br d; 5.6) | 62.77 | 18, 19, 25 |
| 18 | 5.82(br d; 4.7) | 118.65 | 14, 16, 17, 20 |
| 19 | — | 148.10 | |
| 20 | — | 77.69 | |
| 21 | 1.71(m), 1.34(m) | 27.28 | |
| 22 | 2.06(m), 2.02(m) | 21.11 | |
| 23 | 2.80(m) | 49.65 | |
| 24 | 2.65(d m; 4.4), 2.39 (dd; 12.9, 12.9) | 34.72 | 2, 3 |
| 25 | — | 141.63 | |
| 26 | 5.20(br s), 5.03(br s) | 111.66 | 16, 25, 27 |
| 27 | 1.79(br s) | 19.76 | 16, 25, 26 |
| 28 | 1.10(s) | 20.20 | 10, 11, 12, 20 |
| 29 | 1.28(s) | 16.20 | |
| 30 | — | 41.13 | |
| 31 | 6.05(dd; 17.4, 10.6) | 148.79 | 6, 30, 33, 34 |
| 32 | 5.06(dd; 17.3, 1.2), 4.99(dd; 10.6, 1.2) | 110.03 | |
| 33 | 1.41(s) | 28.63 | |
| 34 | 1.41(s) | 28.63 | |

[a]Data were recorded in CDCl$_3$ at 600 and 75.6 MHz, respectively. All selective INEPT correlations represent 2- or 3-bond couplings.

TABLE 3

NMR Spectral Data For Sulpinine C[a]

| C/H | $^1$H | $^{13}$C | HMBC Correlations |
|---|---|---|---|
| 1 | 7.13(br s) | — | 2, 7, 9, 10 |
| 2 | — | 176.59 | |
| 3 | — | 202.41 | |
| 4 | 7.62(d; 8.1) | 129.40 | 3, 5, 6, 8 |
| 5 | 7.32(dd; 8.1, 1.8) | 125.26 | 4, 9, 30 |
| 6 | — | 154.47 | |
| 7 | 6.99(d; 1.7) | 124.97 | 3*, 5, 8, 9, 30 |
| 8 | — | 136.81 | |
| 9 | — | 131.57 | |
| 10 | — | 57.46 | |
| 11 | — | 43.42 | |
| 12 | 2.41(m) 1.89(d m; 11.4) | 24.11 | 11, 13, 14, 28 11, 13, 14, 20 |
| 13 | 2.25(m), 1.70(m) | 27.28 | 11, 14, 19 12, 14 |
| 14 | 4.19(dd; 9.3, 9.0) | 71.11 | 13, 18, 19 |
| 16 | 4.04(br s) | 73.41 | 14, 25, 26, 27 |
| 17 | 3.96(br d; 1.9) | 64.55 | 18, 19 |
| 18 | 3.47(br d; 2.3) | 61.80 | 16, 17 |
| 19 | — | 65.45 | |
| 20 | — | 77.10 | |
| 21 | 1.50(m), 1.21(m) | 28.09 | |
| 22 | 1.76(dd m; 13.4, 3.4), 1.34(m) | 24.37 | 10, 21, 23 |
| 23 | 2.99(m) | 36.05 | 2, 3, 10, 11, 21, 22, 24, 29 |
| 24 | 3.05(dd; 17.8, 4.4), 2.40(dd; 17.8, 4.0) | 47.69 | 3, 9, 10, 22, 23 3, 9, 10, 22, 23 |

TABLE 3-continued
NMR Spectral Data For Sulpinine C[a]

| C/H | $^1$H | $^{13}$C | HMBC Correlations |
|---|---|---|---|
| 25 | — | 140.88 | |
| 26 | 5.13(br s), | 112.48 | 16, 25, 27 |
|    | 5.00(d; 1.6) | | 16, 27 |
| 27 | 1.68(br s) | 19.42 | 16, 25, 26 |
| 28 | 0.99(s) | 18.68 | 10, 11, 12, 20 |
| 29 | 1.55(s) | 16.51 | 2, 10, 11, 23 |
| 30 | — | 41.29 | |
| 31 | 5.93(dd; 17.4, 10.6) | 146.35 | 6, 30, 33-4 |
| 32 | 5.09(dd; 10.6, 0.95), | 112.09 | 30, 31 |
|    | 5.06(dd; 17.4, 0.93) | | 30, 31 |
| 33 | 1.37(s) | 28.00 | 6, 30, 31, 34 |
| 34 | 1.37(s) | 28.00 | 6, 30, 31, 33 |

[a]Data were recorded in CDCl$_3$ at 600 and 75.6 MHz, respectively. The asterisk represents a 4-bond coupling; all other HMBC correlations represent 2- or 3-bond couplings.

The methylene chloride extract of the harvested, ground sclerotia possessed exceptional antiinsectan activity. All five compounds were present within the distinct red band that eluted first from the silica gel column. Although this fraction was complex, the mixture was separated directly into pure compounds by reversed-phase HPLC.

The major component of this fraction, sulpinine A, displayed potent antiinsectan activity. The molecular formula was determined to be C$_{32}$H$_{41}$NO$_4$ (13 unsaturations) by analysis of $^{13}$C NMR and HREIMS data. The proton NMR spectrum and homonuclear decoupling experiments suggested the presence of a 1,2,4-trisubstituted benzene ring, an isoprene unit, and a series of four downfield-shifted proton signals in the region from 3.4 to 4.3 ppm, three of which formed an individual spin system. Examination of HMBC [Bax and Summers, J. Am. Chem. Soc. 108:2093 (1986)] and HMQC [Bax and Subramanian, J. Magn. Res. 67:565 (1986)] results allowed assignment of the aromatic ring as that of an indole prenylated at C-6 and alkyl-substituted at C-2 and C-3. Comparison of the DEPT results and the molecular formula indicated that three exchangeable protons were present. The indole NH proton accounted for one of these. The other two must be OH protons. Thus, two of the six oxygenated carbons must bear hydroxyl groups. Further structure elucidation was hampered by slow decomposition of sulpinine A in CDCl$_3$ solution, failure of various methylene protons to reveal one-bond correlations in XHCORR and HMQC experiments, an inability to acetylate more than one hydroxyl group, and difficulty in defining the spin system involving the four downfield-shifted protons.

A second compound from this same fraction exhibited biological activity and spectral properties similar to those of sulpinine A. Analysis of $^{13}$C NMR and mass spectral data suggested a molecular weight of 583 and a molecular formula of C$_{37}$H$_{45}$NO$_5$. This compound was identified as the known compound penitrem B [de Jesus, et al. supra (1983)] by comparison of its spectral data with published values. Comparison of the spectral data for penitrem B and sulpinine A facilitated the structure elucidation of sulpinine A. Proton and $^{13}$C NMR assignments for sulpinine A are provided in Table 1. Of particular utility was the presence of a set of NMR signals corresponding to the four downfield-shifted protons in sulpinine A. Chemical shift data for the relevant portions of the two molecules are presented below. The proton NMR data is compared below:

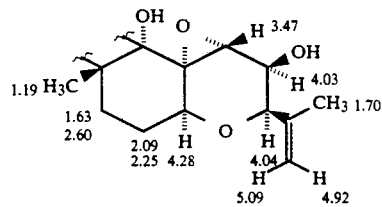

Sulpinine A in methanol

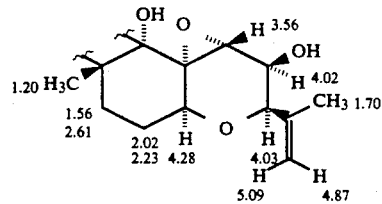

Penitrem B in acetone;

the carbon NMR data is compared below:

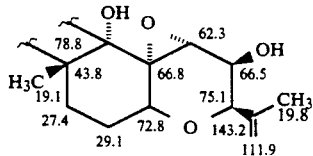

Sulpinine A in methanol

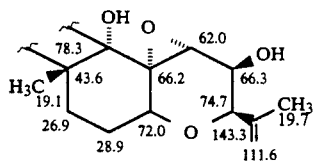

Penitrem B in acetone.

The presence of the epoxide, long-range coupling between H-14 and H-18, and the lack of any vicinal coupling between H-16 and H-17 rationalized the difficulties encountered in assigning the structure of this unit. The failure of the acetylation procedure to correctly indicate the number of hydroxyl group functionalities was explained by the hindered tertiary hydroxyl group at C-20. The remaining assignments were straightforward due to the other skeletal similarities between sulpinine A and the right-hand portion of penitrem B, establishing the structure of sulpinine A.

A third component of the same column fraction, sulpinine B, possessed biological activity of the same magnitude as sulpinine A. The molecular formula of this structurally similar compound was found to contain one less oxygen than sulpinine A by analysis of $^{13}$C NMR and HREIMS data. The EI mass spectrum yielded a base peak of m/z 250 which was the same base peak found in the mass spectrum for sulpinine A. This fragmentation arises from cleavage of the C-21/C-22 and the C-10/C-11 bonds. The intensity and identity of this ion has been noted for other compounds with similar skeletons, such as aflatrem. [Gallagher et al. supra (1980)]. Comparison of the proton spectrum of sulpinine B to that of sulpinine A provided further insight into the structural similarities. The spin systems for the substituted indole and isoprene units were intact as expected from the mass spectral data. The three other methyl singlets and two other terminal methylene protons were also still present. Sulpinine B contained only three proton signals in the region from 3.25–4.75 ppm, rather than four. There was also a new doublet at chemical shift 5.82 ppm. This information, coupled with the changes that were evident in the carbon spectrum—two oxygenated carbon signals were replaced by two vinylic carbon signals—led to the proposal that the epoxide functionality was replaced by a carbon-carbon double bond. This was confirmed by correlated spectroscopy (COSY), HMQC, and a series of selective INEPT experiments [Bax, *J. Magn. Res.* 57:34 (1984)], the data from which are provided in Table 2. In support of this experimental evidence, the known penitrems C and D also possess a similar unit with a C-C double bond in place of the epoxide [de Jesus et al. supra (1983)]. Comparison of the $^{13}C$ NMR chemical shifts for the pyran ring of penitrem C to those of the corresponding carbons of sulpinine B yielded values which were all within one ppm of each other. The only discrepancy was that the shift assignments for carbons 14 and 16 were reversed. In penitrem C, the chemical shifts for the carbons corresponding to positions 14 and 16 of sulpinine B were reported as 80.38 ppm and 74.36, respectively. However, in selective INEPT experiments optimized for 7 Hz, irradiation of $H_3$-27 and $H_3$-26 afforded polarization transfer to 79.07. Thus, this carbon must be at position 16. Furthermore, irradiation of H-16 showed a correlation to 73.65, indicating that C-14 is the correct assignment for this signal. The remaining methylene carbon signals could be assigned by comparison to the corresponding values for sulpinine A.

A fourth metabolite from this column fraction, sulpinine C ($C_{32}H_{41}NO_6$), differed from sulpinine A and sulpinine B only in the presence of additional oxygen atoms. However, the EI mass spectrum did not contain an intense peak at m/z 250. Cursory examination of the proton spectrum revealed many similarities to sulpinine A. The region between 3.25 and 4.75 ppm contained four familiar signals suggesting the presence of the ring system subunit as depicted above. The aromatic region of the proton spectrum exhibited the same 1,2,4-trisubstituted benzene pattern, as well as an NH proton, through the chemical shifts differed significantly from those of sulpinine A. The isoprene unit and the three other methyl singlets were still present, along with a signal shifted from 2.6 to 3.05 ppm. The $^{13}C$ NMR spectrum included the requisite number of oxygenated carbon atoms for the pyran/epoxide ring system; however, the eight carbon signals expected for an indole were not all present. Instead, two new carbonyl signals appeared at 176.59 and 202.41 ppm.

An explanation for the downfield-shifted carbon signals was obtained upon examination of the spectral data presented in Table 3. The assignments for the benzene ring including the 6-prenyl unit were easily made through analysis of HMQC and HMBC experiments. In addition, H-4 displayed a correlation to the signal at 202.41 ppm (C-3). This ketone carbon must therefore be connected to the benzene ring at C-9. The NH proton (H-1) was correlated to C-7 and C-9 of the benzene ring confirming attachment of the nitrogen to C-8. This proton was also correlated to the 176.59 carbon as well as to a quaternary carbon at 57.46 (C-10). The carbonyl signal at 176.59 ppm cannot be a ketone and all other oxygen atoms in the molecule are assigned elsewhere eliminating the possibility of an ester or acid functionality. Therefore, this carbonyl (C-2) must be attached directly to the nitrogen to form an amide group, and C-10 must be alpha to C-2. The methyl group at 1.55 ppm ($H_3$-29) must be attached to the quaternary carbon (C-10) adjacent to the amide group, as it showed a correlation to the amide carbonyl carbon C-2. This methyl also correlated with the methine at C-23. The proton attached to C-23 shows correlations to every carbon that is two to three bonds from it, including the two carbonyl carbons. The placement of the methylene at C-24 adjacent to C-3 was based on HMBC correlations of the protons on C-24 to C-3 and C-9. The final structure could then be assigned as the unprecedented eight-membered ring lactam. This metabolite is clearly an oxidation product of sulpinine A. Because of this relationship, sulpinine C bears the same numbering system as sulpinines A and B even though C-2 and C-3 are no longer connected.

A final compound isolated from this mixture, secopenitrem B, had a molecular weight of 585. The molecular formula indicated the presence of one less unsaturation than penitrem B. By examination of $^{13}C$ and $^{1}H$ NMR data, it was clear that the right hand three-ring subunit was intact in secopenitrem B as in penitrem B, and sulpinines A and C. Evidence for one less oxygenated carbon atom in the $^{13}C$ NMR spectrum suggested that the ether linkage between C-16 and C-18 was severed, since secopenitrem B must have one less ring than penitrem B. Instead of the oxygenated methine carbon at 72.05 ppm there was a new methylene carbon at 29.4 ppm. This supposition proved to be correct following analysis of the results of an HMBC experiment.

ACETYLATION OF SULPININE A

A 2.4-mg sample of Sulpinine A was dissolved in a mixture of pyridine and acetic anhydride (500 μl each). A catalytic amount of DMAP (0.2 mg) was added to facilitate the reaction. The solution was stirred at room temperature for 15 hours, evaporated, and redissolved in 1 ml of chloroform. The resulting solution was extracted with water (3×1 ml) and then dried over magnesium sulfate. Evaporation of the chloroform afforded 2.1 mg of the monoacetylated product.

EXAMPLE 2

Insecticidal Activity Of Sulpinines A-C and Secopenitrem B

The compounds were evaluated by insect bioassays described previously by Dowd in *Entomol. Exp. Appl.* 47:69 (1988). Neonate larvae of *H. zea*, second instar (ca. 0.75 mg) larvae of *C. hemipterus* and adults of *C. hemipterus* were used for all assays. They were obtained from laboratory colonies reared on a pinto bean-based diet at 27° C.±1° C., 40±10% relative humidity, and a 14:10 light:dark photoperiod.

The diet used to rear the insects was based on a standard pinto bean diet for many species, which contains the following ingredients: 120 g dried pinto beans, 43 g wheat germ, 28 g brewer's yeast, 8 g Vanderzant's vitamin mix, 2.8 g ascorbic acid, 1.75 g methyl paraben, 0.9 g sorbic acid, 12 g agar, 2 ml formaldehyde (38%), 1.5 ml of propionic-phosphoric acid solution (42% propionic acid, 4.2% phosphoric acid), and 550 ml water. All dry diet ingredients (except for the pinto beans) were purchased from U.S. Biochemicals Corp. Before use, the beans were soaked in water until saturated (overnight). The agar was added to 250 ml of water and brought to a boil. The other ingredients were blended in a Waring blender until uniformly mixed. The hot agar was added, and blending continued until all ingredients were uniformly mixed.

The pinto bean-based diet thus prepared was added in 5-ml quantities to test tubes. The test tubes were held at 60° C. until chemicals were incorporated to prevent solidification of the diet. A compound of the present invention was added in 125 μl of acetone to the liquid diet to give a final concentration of 100 ppm. Upon addition of the compound, the mixture was removed from the water bath. The chemical was incorporated into the diets by blending vigorously with a vortex mixer for 20 sec. Preliminary observations with colored solutions of both water and acetone indicated uniform incorporation by this method. The diets were dispensed into culture plates and allowed to cool to room temperature. To remove the potentially toxic acetone, the diets were placed in a fume hood for ca. 20 min until slight darkening occurred. The diets were cut into approximately equal sections, and each section was placed into a well of a 24-well immunoassay plate. A single neonate H. zea or five C. hemipterus larvae or adults was added to each well. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 2,4 and 7 days, and the surviving larvae were weighed after 7 days. Each chemical set was tested on a total of 20 larvae. Diet feeding rating for C. hemipterus larvae was based on a scale of 1 (limited to no feeding) to 4 (diet thoroughly tunneled or pulverized [Wicklow et al., supra (1988)].

All five compounds are active against the corn earworm, Helicoverpa zea, formerly known as Heliothis zea. Sulpinines A and B possess potent activity. A 96.0% reduction in weight gain relative to controls after one week was noted for this compound when incorporated into a standard H. zea test diet at 100 ppm. A 10.5% mortality rate was also observed in this assay. Sulpinine B and secopenitrem B cause weight gain reductions comparable to sulpinine A (87.2% and 87.0%, respectively). Sulpinine B and secopenitrem B also induce a mortality rate of 44.4% and 31.6%, respectively. The ring-opened sulpinine C causes a reduction in weight gain of 26.5%. Sulpinine C also induces a feeding reduction of 32.0% in the adults of the fungivorous dried fruit beetle, Carpophilus hemipterus.

EXAMPLE 3

Topical Insecticidal Activity of Sulpinine A and Secopenitrem B

Neonate larvae of H. zea were used for all assays. They were obtained from laboratory colonies reared on pinto bean-based diet at 27° C.±1° C., 40±10% relative humidity, and a 14:10 light:dark photoperiod. A single neonate H. zea was added to each well of a 24-well immunoassay plate. Each larva was treated with a dosage of 2 μg of sulpinine A or secopenitrem B in 0.2 μl acetone per 2 mg larva which was administered from a syringe touching the dorsum of the larva. The larvae were fed the standard pinto bean diet as described in example 2. To prevent desiccation of the diet, the plate was covered by a sheet of parafilm, a sheet of cardboard, and the plastic cover. The cover was secured by two rubber bands, and groups of plates were placed in two polyethylene bags held closely by rubber bands. The plates were held under the same conditions used to rear the insects. Mortality was checked at 4 days, and the surviving larvae were weighed.

Secopenitrem B exhibits significant topical activity against the corn earworm H. zea. Administering this compound at 2 μg per 2 mg insect caused a 66.2% reduction in weight gain of the test insects relative to controls. Sulpinine A exhibited a 54.5% weight reduction in H. zea weight gain under the same test conditions.

EXAMPLE 4

Isolation and Purification of Aflatrem B

Fungal isolates of A. flavus were obtained from the ARS collection at the USDA Center for Agricultural Utilization Research in Peoria, Ill. The sclerotia were prepared by solid substrate fermentation on autoclaved corn kernels using procedures described by Wicklow et al. supra (1988), and were stored at 4° C. until extracted.

Ground A. flavus sclerotia (NRRL 18835, 52.1 g) were exhaustively extracted with hexane, and this extract (268.0 mg) was directly subjected to preparative reversed phase HPLC (8 μm $C_{18}$ column; 2.14×25 cm; 90:10 MeOH-$H_2O$ at 8.4 ml/min) to afford paspalinine (retention time 17 min; 7.5 mg), aflatrem (26 min, 7.8 mg), aflatrem B (32 min, 22.3 mg), nominine (34 min, 2.2 mg), aflavinine (38.5 min, 12.2 mg) and paspaline (66 min, 1.4 mg), along with four other compounds previously isolated from A. flavus sclerotia [Gloer et al. supra (1988) and TePaske et al. supra (1990)].

In determining the properties of aflatrem B, NMR chemical shifts were recorded using the signal for the $CDCl_3$ carbon signal (77.0 ppm) or the residual $CHCl_3$ signal (7.24 ppm) as a reference. Carbon multiplicities were established using a DEPT experiment. One-bond C-H correlations were obtained through an HMQC experiment and long range C-H correlations were obtained through selective INEPT experiments optimized for 4,7, or 10 Hz.

Aflatrem B was obtained as a yellow crystalline solid with the following properties: mp 188°–190° C.; $[α]_D$+77.9° (c=0.011 g/dl); UV (MeOH); 233 (ε18500), 264 (6300), 296 (2700); $^1H$ NMR, $^{13}C$ NMR, and selective INEPT data in Table 1; IR ($CH_2Cl_2$) 3572, 3468, 3060, 2971, 2937, 1690, 1614, 1455, 1275, 894 $cm^{-1}$; EIMS (70 eV): 501 ($M^+$; rel. int. 20), 486 (21), 483 (18), 468 (18), 443 (10), 428 (16), 425 (31), 410 (48), 387 (17), 372 (4), 344 (5), 250 (31), 237 (37), 222 (23), 198 (35), 182 (50), 168 (37), 130 (100); HREIMS, obsd. 501.2877; calcd. for $C_{32}H_{239}NO_4$, 501.2881.

TABLE 4

| | Proton and Carbon NMR Data For Aflatrem B$^a$ | | |
|---|---|---|---|
| C/H | $^1H$ | $^{13}C$ | Selective INEPT Correlations |
| 1 | 7.73 | — | |
| 2 | — | 152.45 | |
| 3 | — | 117.22 | |
| 4 | — | 124.94 | |
| 5 | 7.43(d; 1.5) | 115.32 | 3, 9, 29 |
| 6 | — | 140.11 | |
| 7 | 7.13(dd; 1.5, 8.8) | 119.54 | 5, 9, 29 |
| 8 | 7.27(d; 8.8) | 111.04 | 4, 6 |
| 9 | — | 138.14 | |
| 10 | — | 51.45 | |
| 11 | — | 39.86 | |
| 12ax | 2.69(m) | 26.93 | |

TABLE 4-continued

Proton and Carbon NMR Data For Aflatrem B[a]

| C/H | $^1$H | $^{13}$C | Selective INEPT Correlations |
|---|---|---|---|
| 12eq | 2.26(m) | — | |
| 13ax | 1.82(m) | 21.14 | |
| 13eq | 1.75(m) | — | |
| 14 | — | 104.36 | |
| 15 | 4.32(s) | 87.96 | 14 |
| 16 | — | 197.28 | |
| 17 | 5.86(s) | 117.58 | |
| 18 | — | 169.84 | |
| 19 | — | 77.61 | |
| 20ax | 2.83(m) | 28.25 | |
| 20eq | 2.73 | — | |
| 21ax | 2.45(br dd; 12.5, 10.3) | 27.58 | |
| 21eq | 2.73(m) | — | |
| 22 | 2.83(m) | 48.55 | |
| 23 | 1.97(m) | 33.82 | |
| 23 | 1.92(m) | — | |
| 24 | — | 78.71 | |
| 25 | 1.14(s) | 23.07 | 15, 24, 26 |
| 26 | 1.42(s) | 28.76 | 15, 24 |
| 27 | 1.19(s) | 23.53 | 12, 19 |
| 28 | 1.23(s) | 16.27 | |
| 29 | — | 41.05 | |
| 30 | 6.12(dd; 10.5, 17.3) | 149.01 | 32 |
| 31 | 5.05(br d; 10.5) | 109.87 | |
| 31 | 5.09(br d; 17.3) | — | |
| 32, 33 | 1.48(s) | 28.83, 28.76 | 6, 29, 31, 32, 33 |

[a]Data were obtained in CDCl$_3$ at 360 and 90 MHz, respectively. Carbon assignments are based upon multiplicities, HMQC, and selective INEPT results.

EXAMPLE 5

Insecticidal Activity of Aflatrem B

The compound was evaluated by the procedure described in example 2 using a single neonate *H. zea*. The procedure differed in that a pinto bean-based diet having a final concentration of 200 ppm aflatrem B was prepared.

Aflatrem B exhibits antiinsectan activity against *Helicoverpa zea*. A 57.2% reduction in weight gain relative to controls after one week was noted for aflatrem B when incorporated into a standard *H. zea* diet at 200 ppm.

EXAMPLE 6

Isolation and Purification of 10-Oxo-11,33-dihydropenitrem B

The culture of *A. sulphureus* (NRRL 18838) was obtained from the Agricultural Research Service (ARS) culture collection at the National Center for Agricultural Utilization Research in Peoria, Ill. Production of sclerotia was accomplished by solid substrate fermentation of *A. sulphureus* on autoclaved corn kernels using procedures described by Wicklow et al., supra (1988). The sclerotia were harvested, ground to a powder using a Tecator mill obtained from Perstorp Instrument Co. and stored at 4° C. until extraction.

Powdered sclerotia of *A. sulphureus* (150.0 g) were sequentially extracted with pentane and methylene chloride using a Soxhlet apparatus. A portion (894 mg) of the total methylene chloride extract (1.59 g) was fractionated by silica gel column chromatography. A stepwise gradient from 0–10% (v/v) methanol in chloroform was employed resulting in the elution and collection of a distinct red band at 4% methanol. The fraction that yielded 10-oxo-11,33-dihydropenitrem B eluted immediately after this distinct band. This active fraction (50.1 mg) was further separated by reversed-phase HPLC (92:8 MeOH-H$_2$O) to yield 9.7 mg 10-oxo-11,33-dihydropenitrem B as a light yellow solid.

10-Oxo-11,33-dihydropenitrem B has the following properties: HPLC retention time 8.9 min; $[\alpha]_D$ −78.6° (c=0.002 g/ml); $^1$H NMR, $^{13}$C NMR, HMBC, and NOESY data in Table 5; EIMS (70 eV): m/z 599 (M+; rel. int. 26), 493 (15), 469 (26), 400 (9), 265 (12), 264 (65), 134 (26), 133 (23), 131 (23), 130 (100), 119 (54); HREIMS: obsd. 599.3244; calcd. for C$_{37}$H$_{45}$NO$_6$, 599.3247. The instruments as described in example 1 were used in determining the properties of the compound.

TABLE 5

Spectral Data For 10-Oxo-11,33-dihydropenitrem B[a]

| C/H# | $^1$H | $^{13}$C | HMBC Correlations | NOESY Correlations[c] |
|---|---|---|---|---|
| 2 | — | 155.1 | | |
| 3 | — | 120.8 | | |
| 4 | — | 136.5 | | |
| 5 | — | 125.8 | | |
| 6 | 7.38(d; 8.5) | 118.9 | 4, 7, 8, 9[b], 10 | |
| 7 | 7.18(d; 8.5) | 111.4 | 4[b], 5, 9 | |
| 8 | — | 143.4 | | |
| 9 | — | 122.7 | | |
| 10 | — | 203.8 | | |
| 11 | 2.81(m) | 46.6 | 10, 12, 13, 33 | |
| 12 | 2.27(m) | 34.4 | 13, 14, 33 | 33 |
| 13a | 2.18 | 28.7 | 11, 12, 14, 16 | |
| 13b | 1.91(m) | — | 11, 12, 15 | |
| 14 | 2.77(m) | 50.5 | 4, 13, 15, 16, 34, 35 | 35 |
| 15 | 3.83(dd; 9.2, 9.2) | 35.7 | 4, 5, 9, 11, 12, 14, 16 | 18, 34 |
| 16 | — | 77.3 | | |
| 18 | 4.89(d; 8.2) | 73.2 | 2, 3, 16, 19, 20 | 15, 34, 40 |
| 19 | 2.65(m) | 59.9 | 18, 20, 21, 32, 40 | 39 |
| 20ax | 1.93(m) | 18.8 | 19, 21, 32 | 40 |
| 20eq | 1.77(m) | — | 19, 22 | |
| 21ax | 1.47(m) | 30.5 | 19 | 24 |
| 21eq | 1.74(m) | — | 19, 22 | |
| 22 | — | 78.5 | | |
| 23 | — | 66.7 | | |
| 24 | 3.49(br s) | 62.2 | 25, 26 | 21ax, 36, 39 |
| 25 | 4.04(br s) | 66.5 | 28, 36, 37, 38 | 28 |
| 26 | 4.03(br s) | 75.1 | 23, 24, 26 | |
| 28 | 4.29(dd; 9.2, 8.6) | 72.7 | 23, 24, 29 | 25 |
| 29ax | 2.10(m) | 29.0 | 28, 30 | 39 |
| 29eq | 2.29(m) | — | 23, 28, 30, 31 | |
| 30ax | 2.61(m) | 27.0 | 22, 29, 31, 39 | 40 |
| 30eq | 1.62(m) | — | 22, 28, 29, 31, 32 | |
| 31 | — | 44.0 | | |
| 32 | — | 50.9 | | |
| 33 | 1.14(d; 6.4) | 12.7 | 10, 11, 12 | 12 |
| 34 | 1.55(s) | 19.0 | 14, 16, 35 | 15, 18, 35 |
| 35 | 1.20(s) | 28.7 | 14, 16, 34 | 14, 34 |
| 36 | 1.71(br s) | 19.8 | 26, 37, 38 | 24, 38b |
| 37 | — | 143.2 | | |
| 38a | 5.09(br s) | 111.9 | 26, 36, 37 | |
| 38b | 4.91(br s) | — | 26, 36 | 36 |
| 39 | 1.23(s) | 19.0 | 22, 30, 31, 32 | 19, 24, 29ax |
| 40 | 1.42(s) | 21.2 | 2, 19, 31, 32 | 18, 20ax, 30ax |

[a]Data were recorded in CD$_3$OD at 600 and 75.6 MHz, respectively.
[b]These correlations represent 4-bond couplings; all other HMBC correlations represent 2- or 3-bond couplings.
[c]NOESY correlations between scalar coupled protons have been omitted.

The molecular formula of 10-oxo-11,33-dihydropenitrem B was determined to be C$_{37}$H$_{45}$NO$_6$ by analysis of HREIMS data. This formula is identical to that of penitrem E [de Jesus, et al. supra (1983)]. Penitrem E is hydroxylated at C-15, but otherwise identical to penitrem B. Comparison of the $^{13}$C NMR data for penitrems B and E with those of 10-oxo-11,33-dihydropenitrem B indicated that one methylene and two vinylic carbon signals in the $^{13}$C NMR spectrum of penitrem B appear to be replaced with new methyl, methine, and ketone carbon signals in the $^{13}$C NMR spectrum of 10-oxo-11,33-dihydropenitrem B.

$^{13}$C and $^1$H NMR assignments for 10-oxo-11,33-dihydropenitrem B are provided in Table 5. Carbon-proton one-bond correlations were made by analysis of an HMQC spectrum. By comparing HMBC data obtained for 10-oxo-11,33-dihydropenitrem B with the data published for secopenitrem B and penitrem B, it was determined that the indole nucleus as well as the entire right-hand portion of the molecule (rings F-I) were intact. The location of the ketone carbonyl functionality at C-10 was established on the basis of an HMBC correlation (Table 5) between H-6 and the ketone carbon (C-10). The methyl doublet (for H$_3$-33) also shows a correlation to the ketone carbonyl signal C-10, demonstrating that the methine is directly connected to C-10. In addition, the corresponding methine proton (H-11) shows correlations to C-10, C-12, C-13, and C-33, thereby confirming the location of the CH-CH$_3$ unit. HMBC data indicated that the remainder of the molecule is identical to the corresponding portion of penitrem B.

The relative stereochemistry of 10-oxo-11,33-dihydropenitrem B was deduced by examination of nuclear overhauser enhancement/exchange spectroscopy (NOESY) data and by analogy to penitrem B. Axial and equatorial proton dispositions were assigned based on coupling constants, NOESY correlations, and comparisons to the data for penitrem B. All NOESY correlations are consistent with the relative stereochemistry proposed for penitrem B [de Jesus et al. supra (1983)]. The assignment of the new methyl group (CH$_3$-33) to an equatorial position was based on its NOESY correlation to H-12. This correlation would be unlikely if CH$_3$-33 were in an axial position.

EXAMPLE 7

Insecticidal Activity of 10Oxo-11,33-dihydropenitrem B

The compound was evaluated by the procedure described in example 2. 10-Oxo-11,33-dihydropenitrem B exhibits antiinsectan activity against *Helicoverpa zea* and *Carpophilus hemipterus*. A 95.1% reduction in weight gain relative to controls after one week was noted for the 10-oxo-11,33-dihydropenitrem B when incorporated into a standard *H. zea* diet at 100 ppm. A feeding reduction of 33% was induced in the adults of *C. hemipterus*.

EXAMPLE 8

Isolation and Purification of 14-Hydroxypaspalinine and 14-(N,N-Dimethylvalyloxy)paspalinine Fungal isolates of *A. nomius* (NRRL 13137) were obtained from the ARS collection at the USDA Center for Agricultural Utilization Research in Peoria, Ill. The sclerotia were prepared by solid substrate fermentation on autoclaved corn kernels using procedures described by Wicklow et al. supra (1988), and were stored at 4° C. until extracted.

Ground *A. nomius* sclerotia (16.3 g) were extracted with hexane, followed by chloroform (5×50 ml each). Evaporation of the solvent from the combined chloroform extracts afforded 59.3 mg of a yellow oil. A portion of the extract (49.6 mg) was subjected to reversed-phase semipreparative HPLC (8:2 MeOH:H$_2$O at 2.0 ml/min) to afford 1.6 mg of 14-hydroxypaspalinine having the properties: $^1$H NMR, $^{13}$C NMR, HMBC, and NOESY data, Table 6; EIMS (70 eV): m/z449 (M$^+$; rel. int. 3%), 434 (4), 358 (1), 285 (0.5), 265 (0.6), 212 (2), 182 (10), 168 (89), 130 (9), 100 (14), 44 (65), 43 (26); HREIMS: obsd. 449.2185; calcd. for C$_{27}$H$_{31}$NO$_5$, 449.2202.

*A. nomius* sclerotia (58.9 mg) was Sohxlet-extracted with pentane for 6 days. Filtration and evaporation of the solvent afforded 377.6 mg of a light yellow oil. This residue was subjected to reversed-phase preparative HPLC (85:15 MeOH:H$_2$O at 11.2 ml/min), to obtain 39.6 mg of 14-(N,N-dimethylvalyloxy) paspalinine with the following properties: $^1$H NMR, $^{13}$C NMR, HMBC data, Table 7; UV (MeOH) $\lambda_{max}$228 ($\epsilon$15620), 279(3110); IR (neat) 3399, 2936, 1734, 1690 cm$^{-1}$; FABMS (3-NBA matrix) m/z 577 [(M+H)$^+$, rel. int. 100%], 576 (40), 575 (18), 533 (3.9), 519 (5.2), 449 (2.1), 448 (4.2), 431 (3.8), 390 (4.4), 374 (6.7), 358 (5.2); HRFABMS: obsd. 577.3278; calcd. for C$_{34}$H$_{45}$N$_2$O$_6$(M+H)$^+$, 577.3276.

In determining the properties of the compounds, carbon multiplicities were determined by DEPT experiments, and are consistent with the assignments. 2D-NMR experiments were conducted at 600 MHz ($^1$H dimension). HMBC and HMQC experiments were optimized for $^nJ_{CH}$ values of 8.5 and 135 Hz, respectively. Selective INEPT experiments were optimized for $^nJ_{CH}$=7 Hz. Reversed-phase preparative HPLC was accomplished using a Rainin Dynamax-60A 8μ C$_{18}$ column (21.4 mm×25 cm).

TABLE 6

NMR Data For 14-Hydroxypaspalinine in CDCl$_3$

| Position | $^1$H | $^{13}$C | HMBC Correlations | NOESY Correlations[a] |
|---|---|---|---|---|
| 1 | 7.69(s) | — | 2, 18, 19, 24 | 5, 23 |
| 2 | — | 151.0 | — | |
| 3 | — | 50.5 | — | |
| 4 | — | 40.1 | — | |
| 5ax | 2.68(dd, 12.5, 10.4) | 27.6 | 3, 4, 6, 7 | 25 |
| 5eq | 1.79(ddd, 12.7, 10.0, 8.9) | | 4, 6, 13 | 26 |
| 6ax | 2.84(m) | 28.5 | 4, 5, 7 | 26 |
| 6eq | 2.00(m) | | 4, 7, 12 | |
| 7 | — | 104.7 | — | |
| 9 | 4.30(br s) | 88.1 | 7, 10, 11, 28 | 28, 29 |
| 10 | — | 197.8 | — | |
| 11 | 6.24(s) | 120.3 | 7, 9, 12, 13 | 14 |
| 12 | — | 167.0 | — | |
| 13 | — | 79.3 | — | |
| 14 | 4.25(dd, 10.4, 5.7) | 71.2 | 12, 13, 15, 16 | 11, 16, 26 |
| 15ax | 2.04(ddd; 14.2, 12.4, 10.7) | 31.9 | 3, 13, 14, 16 | 25 |
| 15eq | 2.00(m) | | 3, 13, 14, 16, 17 | |
| 16 | 2.84(m) | 45.2 | 3, 4, 14, 15, 17, 25 | 14, 26 |
| 17eq | 2.71(dd, 13.2, 6.4) | 27.2 | 3, 16, 18 | |
| 17ax | 2.45(dd, 13.2, 10.6) | | 15, 16, 18 | 25 |
| 18 | — | 117.3 | — | |
| 19 | — | 125.0 | — | |
| 20 | 7.41(br d, 6.9) | 118.5 | 18, 19, 22, 24 | 17eq |
| 21 | 7.06(ddd, 7.0, 7.0, 1.6) | 119.7 | 19, 23 | |
| 22 | 7.08(ddd, 7.0, 7.0, 1.6) | 120.7 | 20, 24 | |
| 23 | 7.27(br dd, 7.0, 1.6 | 111.5 | 19, 21, 24 | 1 |
| 24 | — | 139.8 | — | |
| 25 | 1.36(s) | 16.2 | 2, 3, 4, 16 | 5ax, 15, 17ax |
| 26 | 1.21(s) | 23.1 | 3, 4, 5, 13 | 5eq, 6ax, 14, 16 |
| 27 | — | 78.4 | — | |
| 28 | 1.42(s) | 28.8 | 9, 27, 29 | 9, 29 |
| 29 | 1.17 | 23.2 | 9, 27, 28 | 9, 28 |

[a]NOESY correlations for scalar-coupled protons are not included.

TABLE 7
NMR Data For 14-(N,N-Dimethylvalyloxy)paspalinine

| Position[a] | $^1$H | $^{13}$C | HMBC Correlations |
|---|---|---|---|
| 1 | 7.70(s) | — | 2, 18, 19, 24 |
| 2 | — | 150.7 | — |
| 3 | — | 51.2 | — |
| 4 | — | 41.0 | — |
| 5ax | 2.69(m) | 27.7 | 3, 4, 6, 7, 26 |
| 5eq | 1.81(m) | | 4, 6, 13, 26 |
| 6ax | 2.86(m) | 28.6 | 4, 5, 7 |
| 6eq | 1.99(m) | | 4, 7, 12 |
| 7 | — | 104.6 | — |
| 9 | 4.29(s) | 88.4 | 7, 10, 11, 27, 28 |
| 10 | — | 196.1 | — |
| 11 | 5.60(s) | 119.5 | 7, 9, 12, 13 |
| 12 | — | 166.0 | — |
| 13 | — | 79.1 | — |
| 14 | 5.36(dd; 10.5, 5.5) | 74.6 | 1', 15 |
| 15ax | 2.28(m) | 28.9 | 3, 13, 14, 16, 17 |
| 15eq | 2.03(m) | | 3, 13, 14, 16 |
| 16 | 2.86(m) | 45.1 | 3, 4, 14, 17, 25 |
| 17eq | 2.74(m) | 27.2 | 2, 3, 16, 18 |
| 17ax | 2,45(dd, 13.0, 10.7) | | 2, 15, 16, 18 |
| 18 | — | 117.5 | — |
| 19 | — | 125.0 | — |
| 20 | 7.42(br d, 6.8) | 118.6 | 22, 24 |
| 21 | 7.07(m) | 119.9 | 19, 23 |
| 22 | 7.09(m) | 120.9 | 20, 24 |
| 23 | 7.28(br d, 7.0) | 111.6 | 19, 21 |
| 24 | — | 140.0 | — |
| 25 | 1.40(s) | 16.4 | 2, 3, 4, 16 |
| 26 | 1.26(s) | 23.2 | 3, 4, 5, 13 |
| 27 | — | 78.5 | |
| 28 | 1.41(s) | 28.6 | 9, 27, 29 |
| 29 | 1.15(s) | 23.1 | 9, 27, 28 |
| 1' | — | 169.6 | — |
| 2' | 2.73(br d, 10.0) | 74.4 | 1', 3', 4', 5', 6', 7' |
| 3' | 2.06(m) | 27.3 | 1', 2', 4', 5' |
| 4' | 0.96(d, 6.6) | 19.1 | 2', 3', 5' |
| 5' | 0.94(d, 6.6) | 20.0 | 4' |
| 6'/7' | 2.33(s) | 41.6 | 2', 6', 7' |

[a]Axial and equatorial assignments are based on comparison with data from 14-Hydroxypaspalinine.

On the basis of HREMIS and $^{13}$C NMR data, 14-hydroxypaspalinine was determined to possess the molecular formula $C_{27}H_{31}NO_5$. This formula differed from that of paspalinine by the addition of one oxygen atom. As expected, the NMR data revealed close similarities between the two compounds, specifically indicating that one of the five methylene carbons of paspalinine is replaced by an hydroxylated methine (71.2 ppm) in 14-hydroxypaspalinine. The proton spin systems in 14-hydroxypaspalinine were identified by analysis of a $^1$H-$^1$H COSY spectrum recorded at 600 MHz. Although these data showed that the position of hydroxylation could not be C-17 (the proton signal is a doublet of doublets), they did not unambiguously eliminate the four other possible positions, so further information was required. Shift assignments for carbons bound to hydrogen atoms were established on the basis of HMQC [Bax and Subramanian, supra (1986)]. The remaining carbon NMR assignments and the organization of the spin systems were determined with the aid of an HMBC experiment [Bax and Summers, supra (1986)] as summarized in Table 6. HMBC correlations of the methine proton at 4.25 ppm with signals for carbons 12, 13, 15, and 16 indicated the secondary alcohol group location at position 14. All other HMBC correlations are consistent with the proposed structure, and the remainder of the NMR and mass spectral data for this compound support the assignment of the structure as shown.

The relative stereochemistry at the new chiral center was established through analysis of NOESY data and $^1$H NMR J-values as shown in Table 6. In the NOESY experiment, correlations of H-14 with H-16 and H$_3$-26 were observed. In addition, the signals for H-16 and H$_3$-26 showed correlations to H-14 and to each other. These data provide evidence for a 1,3,5-triaxial arrangement of protons 14, 16 and the methyl group H$_3$-26, indicating the relative stereochemistry at position 14 as shown. This stereochemistry is consistent with the J-values observed for H-14, which include an axial-axial coupling with H-15$_{ax}$ (10.7 Hz). The relative configurations at the other chiral centers are the same as those of paspalinine, and the remainder of the NOESY data support this assignment.

Proton and carbon NMR spectra for 14-(N,N-dimethylvalyloxy)paspalinine ($C_{34}H_{44}N_2O_6$ based on HRFABMS) contained signals that matched closely with those for 14-hydroxypaspalinine. The only significant differences were a downfield shift of H-14 (from 4.25 to 5.36 ppm), an upfield shift of H-11 (from 6.24 to 5.60 ppm), and the presence of resonances accounting for the additional carbon atoms and protons indicated by the molecular formula. These observations suggested that 14-(N,N-dimethylvalyloxy)paspalinine differed from 14-hydroxypaspalinine by acylation at the 14-OH with a $C_7H_{14}NO$ unit, and were verified by analysis of COSY, HMQC, and HMBC data for 14-(N,N-dimethylvalyloxy)paspalinine. The $^{13}$C NMR signals associated with the acyl subunit consisted of a carboxyl carbon, four methyl carbons (two bound to nitrogen), and two methine carbons. $^1$H NMR and COSY data demonstrated that the two methine protons are coupled to each other, and that the upfield methine (2.06 ppm) is part of an isopropyl group. HMBC correlations of the downfield methine proton (2.73 ppm) with the carboxyl, N-methyl, and isopropyl group signals, and correlation of the isopropyl methine with the carboxyl carbon signal, indicated that the acyl group is an N,N-dimethylvalyl unit. Petit et al. [*J. Am. Chem. Soc.* 113:6692 (1991)] describe the natural occurrence of the N,N-dimethylvalyl unit as an amino acyl unit in the dolastatins, a family of small peptide antineoplastic agents isolated from sea hares.

The site of connection of the acyl group to the hydroxypaspalinine core structure was determined based on the downfield shift of the H-14 resonance in 14-(N,N-dimethylvalyloxy)paspalinine compared with the non-acylated compound 14-hydroxypaspalinine. This connection was confirmed after analysis of a selective INEPT experiment [Bax, supra (1984)], which afforded a 3-bond correlation of the H-14 resonance to the carboxyl carbon signal of the N,N-dimethylvalyl group (169.6 ppm).

EXAMPLE 9

Insecticidal Activity of 14-Hydroxypaspalinine and 14-(N,N-Dimethylvalyloxy)paspalinine The compounds were evaluated by the procedure described in example 2 using a single neonate *H. zea*. 14-Hydroxypaspalinine and 14-(N,N-dimethylvalyloxy)paspalinine cause a 91% and 82% reduction in weight gain respectively relative to controls after one week when incorporated into a standard *H. zea* diet at 100 ppm.

While the invention is susceptible to various modifications and alternative forms, specific embodiments thereof have been shown by way of example and were herein described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

We claim:

1. A substantially pure indole selected from the group consisting of:

secopenitrem B:

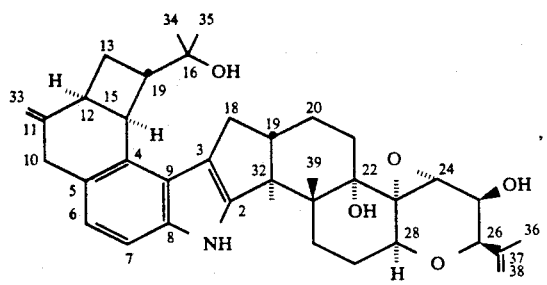

aflatrem B:

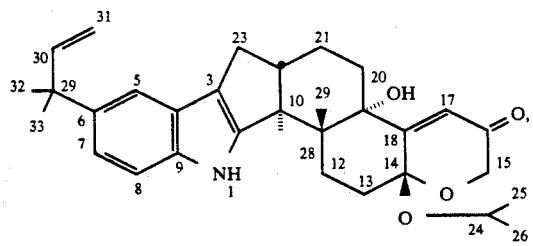

14-hydroxypaspalinine:

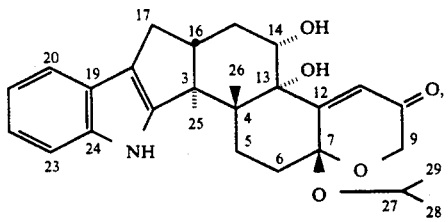

and 14-(N,N-dimethylvalyloxy)paspalinine:

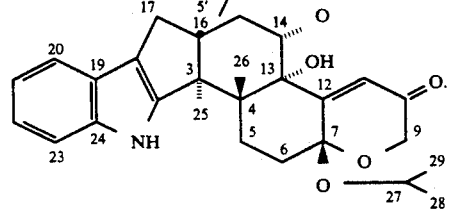

2. A composition for controlling insects comprising: an insecticide selected from the group consisting of aflatrem B, secopenitrem B, 14-hydroxypaspalinine, and 14-(N,N-dimethylvalyloxy)paspalinine; and an inert carrier.

3. The composition of claim 2 including an amount of the insecticide effecting insects of the Lepidoptera species.

4. The composition of claim 2 including an amount of the insecticide effecting *Helicoverpa zea*.

5. A method of controlling insects comprising applying an effective amount of an insecticide selected from the group consisting of aflatrem B, secopenitrem B, 14-hydroxypaspalinine, and 14-(N,N-dimethylvalyloxy)paspalinine to a locus of insects.

6. The method of claim 5 wherein the insects are Lepidoptera species.

7. The method of claim 5 wherein the insects are *Helicoverpa zea*.

* * * * *

UNITED STATES PATENT AND TRADEMARK OFFICE
CERTIFICATE OF CORRECTION

PATENT NO. : 5,227,396  Page 1 of 4
DATED : July 13, 1993
INVENTOR(S) : Laasko et al It is certified that error appears in the above-indentified patent and that said Letters Patent is hereby corrected as shown below:

Col. 2, lines 56-65; and Col. 21, lines 35-45:

Replace "                                                                      "

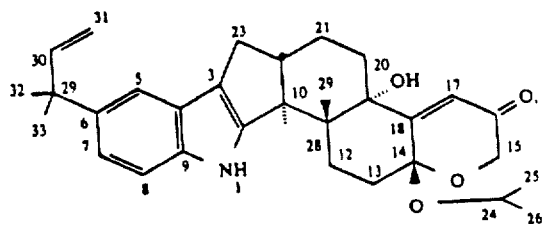

With  --                                                                   --

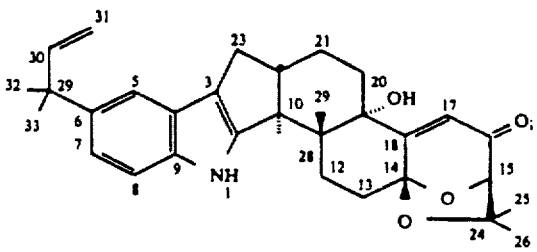

UNITED STATES PATENT AND TRADEMARK OFFICE
CERTIFICATE OF CORRECTION

PATENT NO. : 5,227,396

DATED : July 13, 1993

INVENTOR(S) : Laasko et al

Page 2 of 4

It is certified that error appears in the above-indentified patent and that said Letters Patent is hereby corrected as shown below:

Col. 3, lines 1-10 and Col. 22, lines 1-10

Replace  "

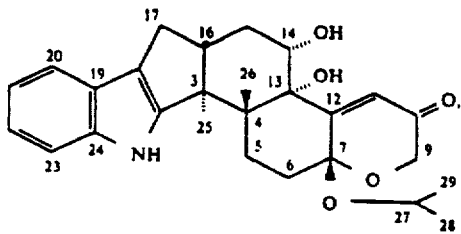

With  --

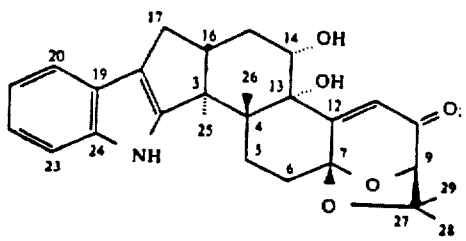

--

UNITED STATES PATENT AND TRADEMARK OFFICE
CERTIFICATE OF CORRECTION

PATENT NO. : 5,227,396
DATED : July 13, 1993
INVENTOR(S) : Laasko et al

Page 3 of 4

It is certified that error appears in the above-indentified patent and that said Letters Patent is hereby corrected as shown below:

Col. 3, lines 15-29; and Col. 22, lines 15-28:

Replace "  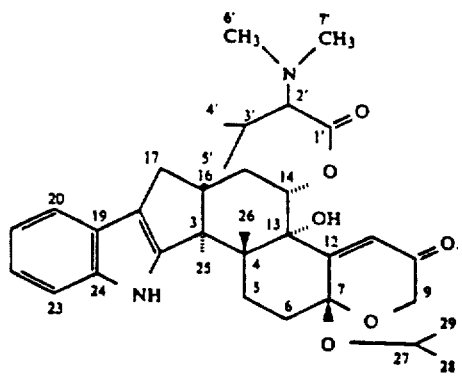  "

UNITED STATES PATENT AND TRADEMARK OFFICE
CERTIFICATE OF CORRECTION

PATENT NO. : 5,227,396
DATED : July 13, 1993
INVENTOR(S) : Laasko et al

It is certified that error appears in the above-indentified patent and that said Letters Patent is hereby corrected as shown below:

With    --    --

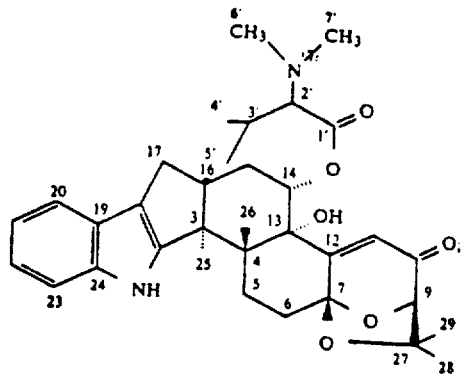

Signed and Sealed this

Twenty-sixth Day of April, 1994

Attest:

BRUCE LEHMAN

Attesting Officer     Commissioner of Patents and Trademarks